United States Patent [19]

Franco et al.

[11] Patent Number: 4,827,078

[45] Date of Patent: * May 2, 1989

[54] PROCESS FOR EXTRACTING PARAFFINS FROM THEIR MIXTURES WITH ALKANESULFONIC ACIDS

[75] Inventors: Cosimo Franco, Locri; Gerardo Carrillo; Lucio Faggian, both of San Donato Milanese, all of Italy

[73] Assignees: Eniricherche, S.P.A., Milan; Enichem Augusta, S.P.A., Palermo, both of Italy

[ * ] Notice: The portion of the term of this patent subsequent to Jan. 17, 2006 has been disclaimed.

[21] Appl. No.: 71,926

[22] Filed: Jul. 10, 1987

[30] Foreign Application Priority Data

Jul. 23, 1986 [IT] Italy ............................... 21225 A/86

[51] Int. Cl.$^4$ ........................................ C07C 143/24
[52] U.S. Cl. ..................... 585/864; 585/833; 208/24; 260/505 P
[58] Field of Search ..................... 208/24, 27; 585/833, 585/864; 260/505 A, 505 P, 505 S

[56] References Cited

U.S. PATENT DOCUMENTS

| | | | |
|---|---|---|---|
| 2,228,598 | 1/1941 | Fox | 260/513 |
| 2,875,257 | 2/1959 | Thompson | 260/505 P |
| 3,033,898 | 5/1962 | Bray | 260/505 P |
| 3,681,442 | 8/1972 | Bloch et al. | 585/864 |
| 4,269,789 | 5/1981 | Zornes | 260/505 P |
| 4,361,520 | 11/1882 | Luetzelschwab | 260/505 P |

FOREIGN PATENT DOCUMENTS 1532207 11/1978 United Kingdom .

*Primary Examiner*—Glenn Caldarola
*Attorney, Agent, or Firm*—Morgan & Finnegan

[57] ABSTRACT

In preparing alkanesolfonic acids by sulfoxidation of n-paraffins containing between 12 and 18 carbon atoms, using ultraviolet radiation to initiate the reaction (light-water process), a mixture is obtained which spontaneously allows a substantial part of the unconverted n-paraffins to phase separate from a phase containing the remainder of the reaction mixture containing the alkanesulfonic acids together with water, sulfuric acid and n-paraffins.

The remainder of the mixture is fed with one or more alcohols having four or less than four carbon atoms, preferably isopropanol, to form a two-phase mixture.

The two-phase mixture is extracted with supercritical carbon dioxide, which extracts the n-paraffins, these being recycled to the sulfoxidation process.

The paraffin-free product is suitable for preparing alkane-sulfonates of the desired type by neutralization with suitable bases.

6 Claims, 1 Drawing Sheet

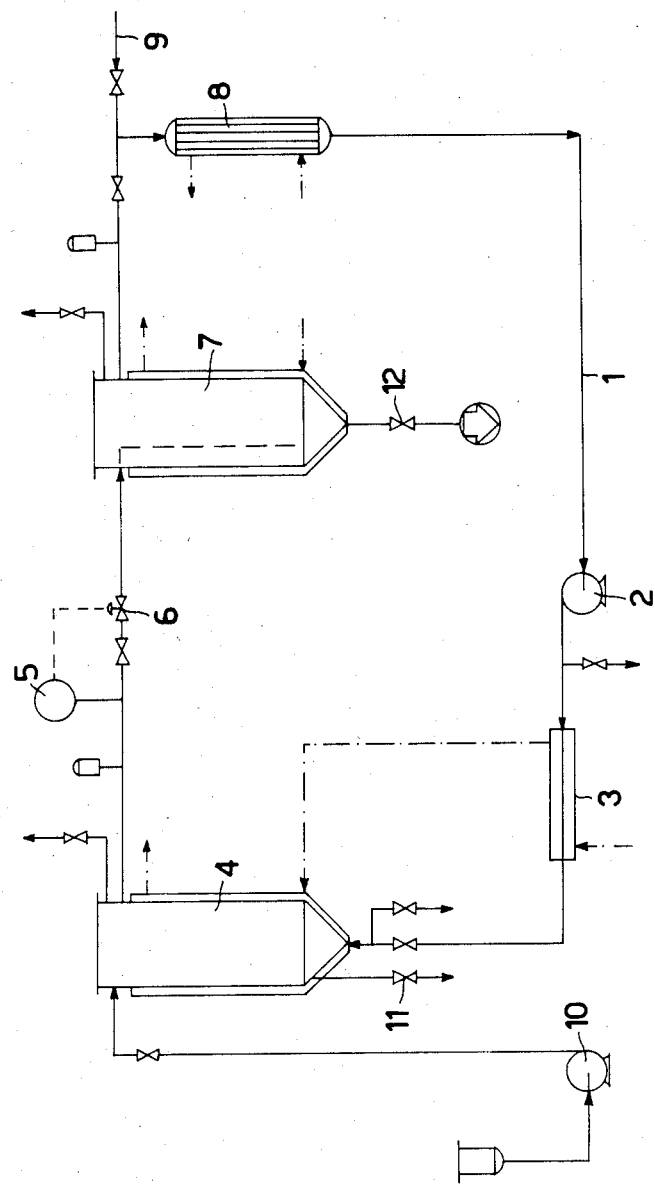

PROCESS FOR EXTRACTING PARAFFINS FROM THEIR MIXTURES WITH ALKANESULFONIC ACIDS

This invention relates to a process for extracting paraffins from their mixtures with alkanesulfonic acids. In the description the term alkanesulfonic acid is synonymous with paraffinsulfonic.

Alkanesulfonic acids containing between 12 and 18 carbon atoms are generally prepared by sulfoxidation of $C_{12}$–$C_{18}$ n-paraffins with sulfur dioxide ($SO_2$) and oxygen ($O_2$) using ultraviolet (UV) radiation for reaction initiation. The reaction product obtained from the sulfoxidation reactor consists of a mixture containing small percentages of alkanesulfonic acids, water and sulfuric acid ($H_2SO_4$), but mostly unreacted n-paraffins.

Most of the paraffins can be easily separated from said mixture, but a substantial fraction of them remains together with the $H_2SO_4$, the water $H_2O$ and the alkanesulfonic acids.

It is important to note that the paraffins must be separated to the maximum possible extent not only for obvious economic reasons, but also because their presence in alkanesulfonic acids is undesirable.

The known art gives suggestions for separating said paraffins from the rest of the $H_2SO_4$, alkanesulfonic acid and $H_2O$ mixture, one of these suggestions being contained in European patent application 131,913, in particular in Example 1, according to which the mixture containing alkanesulfonic acids, unreacted paraffins, $H_2O$ and $H_2SO_4$ is treated with isopropanol in a quantity of 15%, to separate the mixture into three distinct phases, the upper one essentially consisting of paraffins, the lower one consisting of $H_2O$, $H_2SO_4$ and isopropanol, and the intermediate one containing alkanesulfonic acids, $H_2SO_4$, $H_2O$, paraffins and isopropanol. The intermediate phase is then mixed with methylene chloride to separate an aqueous $H_2SO_4$ phase containing isopropanol and a little methylene chloride from a phase containing alkanesulfonic acids, paraffins, water, methylene chloride and $H_2SO_4$, this being neutralized with soda and concentrated, and finally evaporated at a temperature of up to 200° C. to separate the paraffins.

This procedure for removing the paraffins is obviously complicated, and notwithstanding its various extraction stages it is still necessary to use high-temperature treatment at the end, which in all cases damages the product obtained.

With the known process it is therefore not possible to prepare free alkanesulfonic acids or their salts with weak bases, as these are unstable at high temperature.

It has been surprisingly found that the previously described drawbacks of the known art regarding the separation of n-paraffins can be obviated in a very simple manner by mixing the mixture originating from the n-paraffin sulfoxidation reactor, after removing its dissolved sulfur dioxide by ($CO_2$) by known means, with limited quantities of alcohols containing four or less than four carbon atoms, until a two-phase mixture is formed, and then extracting the two-phase mixture which supercritical $CO_2$.

The present invention provides a process for extracting paraffins from their mixtures with alkanesulfonic acids, comprising after previously removing excess $SO_2$, decanting the reaction product originating from a reaction of $C_{12}$–$C_{18}$ n-paraffin sulfoxidation by $SO_2$ and $O_2$ in the presence of UV radiation and $H_2O$ at a temperature of between 25° and 50° C. in order to separate most of the unreacted n-paraffins from the mixture of the reaction mixture. The remaining phase of the reaction is mixed with an aliphatic alcohol containing four or less than four carbon atoms, preferably isopropanol, characterized in that the aliphatic alcohol is used in the quantity necessary to form a two-phase mixture. The two-phase mixture is then extracted with $CO_2$ under supercritical conditions, so separating the paraffins from the alkanesulfonic acids and from the $H_2SO_4$ and the $H_2O$.

The resultant mixture can then be neutralized in known manner with chosen bases, to thus obtain alkanesulfonates of the desired type.

If desired, the $H_2SO_4$ can be separated from the paraffin-free alkanesulfonates by known methods, such as mixing with suitable substances or precipitation to form insoluble salts.

The alcohol used is preferably isopropanol, and the quantity of alcohol used to form the two-phase mixture according to the invention is such that its concentration therein ranges from 3 to 8.5% by weight, and is preferably about 5% by weight.

The conditions under which extraction with supercritical $CO_2$ is carried is at a temperature of between 32° and 80° C., a pressure of between 75 and 350 bar, and a weight ratio of $CO_2$ used for extraction to alkanesulfonic acids of between 1:1 and 50:1.

Some examples are given hereinafter in order to better illustrate the invention, but without intending to limit it thereto or thereby.

EXAMPLE 1

The laboratory extraction apparatus shown diagrammatically in the FIGURE was used.

It consists of a refrigeration cycle for condensing $CO_2$ in heat exchanger 8. The liquid $CO_2$ is pumped by diaphragm pump 2 to preheater 3 and then to the extractor 4. The temperature of preheater 3 and extractor 4 is maintained constant and at the same value by circulating $H_2O$ from a temperature-controlled bath. The pressure in extractor 4 is kept constant at the required value by the controller 5 and control valve 6.

The $CO_2$ containing the products extracted from the crude mixture fed into extractor 4 passes through control valve 6 and leaves the supercritical fluid in separator 7, where the $CO_2$ evaporates and is condensed in heat exchanger 8 and is returned to the described cycle, whereas the extract remains in separator 7. Any required make-up $CO_2$ is fed into the cycle at inlet 9.

Separator 7 is provided with two diametrically opposite sight glasses for visually checking the level.

This is kept constant by adjusting the temperature of the $H_2O$ originating from a second temperature-controlled bath. The pressure in separator 7 is kept constant by a pressure switch which operates the refrigeration cycle.

Extractor 4 is filled with stainless steel packing held down by a demister.

Pump 10 is used for continuous operation to feed the crude product to be extracted. In this case, the refined product is discharged through valve 11.

124.3 g of crude mixture (from which decantable n-paraffins and $SO_2$ have been removed) containing:
$C_{12}$–$C_{18}$ alkanesulfonic acids; 24.74% by weight
$C_{12}$–$C_{18}$ n-paraffins; 26.46% by weight
$H_2O$; 40.94% by weight
$H_2SO_4$; 7.86% by weight were fed into the extractor 4, together with 6.4 g of isopropyl alcohol.

Extractor 4 was temperature-controlled at 45° C., and $CO_2$ was then fed in at a throughput of 1.46 kg/h, maintaining the pressure in extractor 4 at 200 bar. After 1 hour of extraction, $CO_2$ feed was suspended and the product contained in extractor 4 was discharged and analysed. The paraffin quantity extracted was found to be 96% of that present in the crude product feed.

EXAMPLE 2 (Comparative, without isopropanol addition)

123.9 g of a crude, alkanesulfonic acid mixture having the same composition as in Example 1 were extracted with supercritical $CO_2$ under the conditions and for the time stated in Example 1.

Analysis of the refined product showed that the paraffins had been extracted to an extent of 67.5% of the quantity present in the crude product feed.

We claim:

1. In a process for extracting paraffins from a reaction mixture of paraffins with alkanesulfonic acids, where said reaction mixture is obtained by sulfoxidation of n-paraffins with sulfur dioxide and oxygen in the presence of ultraviolet radiation and water at a temperature of between 25°–50° C., comprising the steps of;
   (a) removing excess sulfur dioxide from said reaction mixture;
   (b) decanting said reaction mixture to separate most of the unreacted n-paraffins;
   (c) mixing the remainder of said reaction mixture with a sufficient amount of an aliphatic alcohol containing up to four carbon atoms said aliphatic alcohol being preferably isopropanol, characterized in that the aliphatic alcohol is used in the quantity necessary to form a two-phase mixture; and
   (d) extracting said two-phase mixture with carbon dioxide under supercritical conditions to extract the paraffins from said reaction mixture.

2. A process as claimed in claim 1, wherein the alcohol quantity required to form the two-phase mixture is such as to obtain an alcohol concentration in the mixture of between 3% and 8.5% by weight.

3. A process as claimed in claim 2, wherein the mixture has an alcohol concentration of about 5% by weight.

4. A process as claimed in claim 1, wherein the conditions under which extraction with supercritical $CO_2$ is carried out are a temperature of between 32 and 80 degrees centigrade and a pressure of between 75 and 350 bar.

5. A process as claimed in claim 1, wherein the weight ratio of carbon dioxide to said two-phase mixture is between 1:1 and 50:1.

6. A process as claimed in claim 1, wherein the extracted, paraffin-free alkanesulfonic acid mixture is neutralized with a suitable base.

* * * * *